United States Patent
Kayyali

[11] Patent Number: 6,038,477
[45] Date of Patent: Mar. 14, 2000

[54] MULTIPLE CHANNEL NERVE STIMULATOR WITH CHANNEL ISOLATION

[75] Inventor: Hani A. Kayyali, Shaker Heights, Ohio

[73] Assignee: Axon Engineering, Inc., Garfield Heights, Ohio

[21] Appl. No.: 09/219,050

[22] Filed: Dec. 23, 1998

Related U.S. Application Data

[60] Provisional application No. 60/100,874, Sep. 17, 1998.
[51] Int. Cl.[7] .................................................. A61N 1/32
[52] U.S. Cl. ................................ 607/72; 607/2; 607/118; 128/901
[58] Field of Search ..................... 607/2, 46, 63, 607/72, 39, 40, 115–118; 128/901, 908

[56] References Cited

U.S. PATENT DOCUMENTS

| | | | |
|---|---|---|---|
| 3,727,616 | 4/1973 | Lenzkes | 607/59 |
| 4,608,985 | 9/1986 | Crish et al. | 607/74 |
| 5,041,974 | 8/1991 | Walker et al. | 607/63 |

Primary Examiner—Kennedy J. Schaetzle
Attorney, Agent, or Firm—Jerrold J. Litzinger

[57] ABSTRACT

A multiple channel stimulator for applying electrical impulses to nerves of a mammal using a single power supply to drive a plurality of channels which are selectively activated to apply electrical impulses to nerve trunks through cuff electrodes. As a channel is activated, an isolation resistor in that channel is shorted out, providing a path of low resistance in that channel compared to the other channels, insuring that any leakage current or cross currents between channels is minimized, whereby improving the performance of the stimulator.

18 Claims, 7 Drawing Sheets

MULTIPLE CHANNEL NERVE STIMULATOR WITH CHANNEL ISOLATION

CROSS REFERENCE TO RELATED APPLICATIONS

This is a utility patent application taking priority from provisional patent application Ser. No. 60/100,874 filed Sep. 17, 1998, which is incorporated herein in its entirety by reference.

BACKGROUND OF THE INVENTION

1. Field of the Invention

The present invention relates generally to the biomedical arts, and, in particular, to an improved multi-channel device which finds particular application in introducing a string of artificially generated antidromic pulses on the nerve trunk for collision blocking orthodromic pulses moving in the opposite direction along the nerve trunk and will be described with particular reference thereto. It is to be appreciated, however, that the invention may have broader applications and may apply electrical signals on nerve trunks for other purposes.

2. Description of the Related Art

Heretofore, various techniques have been used to block nerve pulses passing along a nerve trunk. A common blocking technique was the application of DC currents on the nerve trunk. However, it has been found that the application of DC currents can be expected to cause nerve damage.

To eliminate the DC current induced nerve damage, others have suggested using an oscillating current such that the induced electrical current flowed alternately in both directions along the nerve trunk. It has been found that the application of high frequency stimulation blocks the passage of nerve signals therethrough. However, it appears that high frequency stimulation may, in effect, be overdriving neuromuscular junctions and depleting the neurotransmitter at the terminal end. That is, rather than blocking the passage of nerve stimuli on the nerve fiber or axon, the high frequency stimulation techniques may be overworking the nerve terminal to the point of exhaustion causing a failure of proper functioning.

Yet another blocking technique utilized a three electrode cuff which included a dielectric sleeve having a passage through which the nerve trunk passes. Three annular electrodes were arranged within the sleeve. A cathode was positioned near the center of the passage and a pair of anodes were positioned to either side. A signal generator was connected with the electrodes to apply an electrical pulse train that induced antidromic pulses on the nerve trunk. Each pulse of the pulse train included a rapid rise to a preselected amplitude, a 100 to 3000 microsecond plateau, and an exponential decay back to zero. This pulse train induced artificially generated antidromic pulses on the nerve trunk which traveled unidirectionally in the opposite direction to the normal pulse flow. The artificially generated antidromic pulses collided with and blocked further propagation of natural orthodromic pulses moving in the other direction on the nerve trunk. However, the application of a series of pulses of common polarity, again has been found to cause damage to neural tissues.

To eliminate this nerve damage, others have suggested applying a low amplitude, relatively long duration rectangular wave pulse of opposite polarity between each pulse of the above-described pulse train. The opposite polarity of the rectangular wave pulse balanced the net charge flow caused by the primary pulse. However, it has been found that at an upper limiting frequency, the sudden polarity change still tends to depolarize the nerve cell and cause transmission in the wrong direction. This tendency to generate artificial orthodromic pulses, of course, was undesirable. For example, if the antidromic blocking pulses were utilized to block stray excitation pulses moving toward a paralyzed patient's spastically contracted sphincter muscle over which control had been lost, the stray orthodromic pulses would cause undesired activation of the muscles of micturition.

U.S. Pat. No. 4,608,985 provides a system for selectively blocking orthodromic action potentials passing along the nerve trunk. The system includes an electrode cuff including a cathode disposed around the nerve trunk and a dielectric shield disposed encircling the electrode and the nerve trunk to both sides of the electrode. An anode is electrically associated with body tissue such that electrical current flows from the anode through the body tissue and nerve trunk to the cathode. A signal generator is operatively connected with the cathode and anode for cyclically generating electrical pulses. Each pulse cycle includes a first polarity pulse which rises abruptly to a first preselected amplitude, retains the amplitude for a preselected duration, and decays smoothly from the amplitude. Each cycle further includes an opposite polarity phase whose leading edge is a smooth continuation of the first polarity pulse decaying trailing edge. The opposite polarity pulse rises smoothly to a magnitude whose absolute value is less than the first polarity pulse magnitude and which is too low to trigger action potentials. The opposite polarity pulse is substantially longer than the first polarity pulse such that the charge flow during the first and opposite polarity pulse is opposite but generally equal.

Although the system described in the aforementioned patent has been found to be adequate for sacral root stimulation, its original design was intended for percutaneous type of stimulation where the connection between the stimulator and the electrodes is made outside of the body, with the electrode leads penetrating the skin from outside of the body. Such a percutaneous system is prone to infections, lead breakage, and difficulty in maintaining a reliable connection between the leads and the stimulator due to patient movement. Thus, an implantable system is often desirable for many applications in the field of functional electrical stimulation, especially those which require long term stimulation.

The major obstacle which makes it difficult to transform this system from a percutaneous to an implantable device lies in the fact that the circuitry for providing stimulation to each sacral root must be kept isolated. This isolation can be maintained by the use of separate power supplies (batteries) for each channel. Thus, in a device which stimulates six sacral roots, the system employs six separate batteries to provide six isolated output channels. A direct translation of this percutaneous device means that an implantable device must also use six batteries in order to achieve isolation. The use of six batteries would increase the size and weight of an implantable device such that the device may be impractical.

The importance of isolated output channels in a device using a single power supply stems from the fact that stimulation via non-isolated outputs has shown a decreased ability to selectively stimulate the proper sacral roots when compared to isolated outputs. This is due to the leakage currents which exist in non-isolated systems that create unwanted current pathways between the nerve fibers, potentially causing unwanted nerve excitation and damage to the electrodes and also the tissue.

The present invention provides a new and improved device which can overcome the above referenced problems.

SUMMARY OF THE INVENTION

It is therefore an object of the present invention to provide a device having electrical isolation between output channels of a multiple channel nerve stimulator.

It is also an object of the present invention to provide a circuit design for a multi-channel nerve stimulator which minimizes leakage currents between channels.

It is a further object of the present invention to provide a device which may be easily implanted beneath the skin of a patient.

These and other objects of the present invention are accomplished by a novel multiple channel nerve stimulator having a single power supply, a plurality of channels coupled to the power supply, and control means which reduces the resistance in the active channel such that any leakage current to the inactive channels is minimized.

DETAILED DESCRIPTION OF THE PREFERRED EMBODIMENTS

Figure 1:
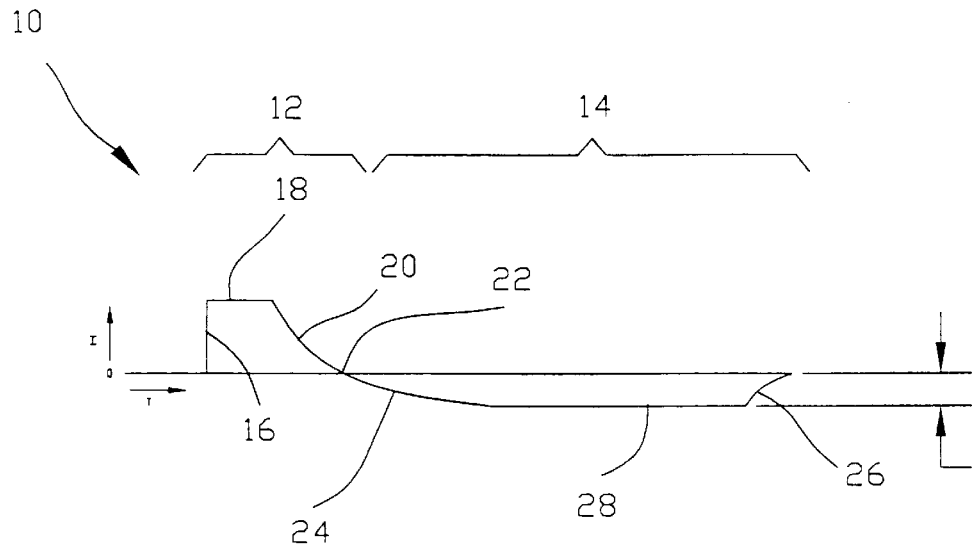
FIG. 1 is a graphic representation of the quasitrapezoidal waveform generated by the stimulator circuitry of the present invention.

Referring more particularly to FIG. 1 of the drawings, a waveform 10 is shown which has been proven to be very effective in the stimulation of sacral nerve roots without undesired muscle activation or tissue damage. Waveform 10, which is sometimes referred to as a quasitrapezoidal pulse, includes a first portion 12 having a first polarity or current direction and a second portion 14 having a second or opposite polarity or current direction. First portion 12 includes a leading edge 16 which rises rapidly to a preselected amplitude which reaches a plateau phase or portion 18 which is maintained for a predetermined duration. After this predetermined duration, plateau phase 18 decays exponentially along on exponential decay portion 20, which reaches zero at a crossover point 22.

In a second pulse portion 14, the current changes polarity and increases in amplitude along an exponential current increase portion 24. At the interface or crossover point 22, the one polarity decay portion 20 and the opposite polarity increase portion 24 have a smooth discontinuity free transition. Although the one polarity decay and the other polarity increase portions follow a common curve, they may follow different smooth curves provided there is substantially no discontinuity along the combined decay and opposite polarity increase portions. The opposite polarity increase portion reaches a steady state amplitude 26 and holds the steady state amplitude for a steady state duration 28 until the beginning of the next cycle. The opposite polarity waveform 28 may/may not quickly return to zero amplitude along an edge 29. Edge 29 is brief and may approach a sharp path. The opposite polarity waveform 28 may not return to zero amplitude and thus 28 may be contiguous with the beginning of the next cycle.

The opposite polarity current amplitude is sufficiently small that the reverse polarity current minimizes the possibility of inducing action potentials on the wave trunk. The magnitude of the opposite polarity amplitude is selected such that the total current flow in the first and second portions 12 and 14 is equal but opposite. In this manner, there is no net charge transfer. It is to be appreciated that opposite polarity current pulses or portions of various shapes may be utilized provided the amplitude remains low and there are substantially no discontinuations along the path described by waveform portions 20 and 24.

Figure 2:
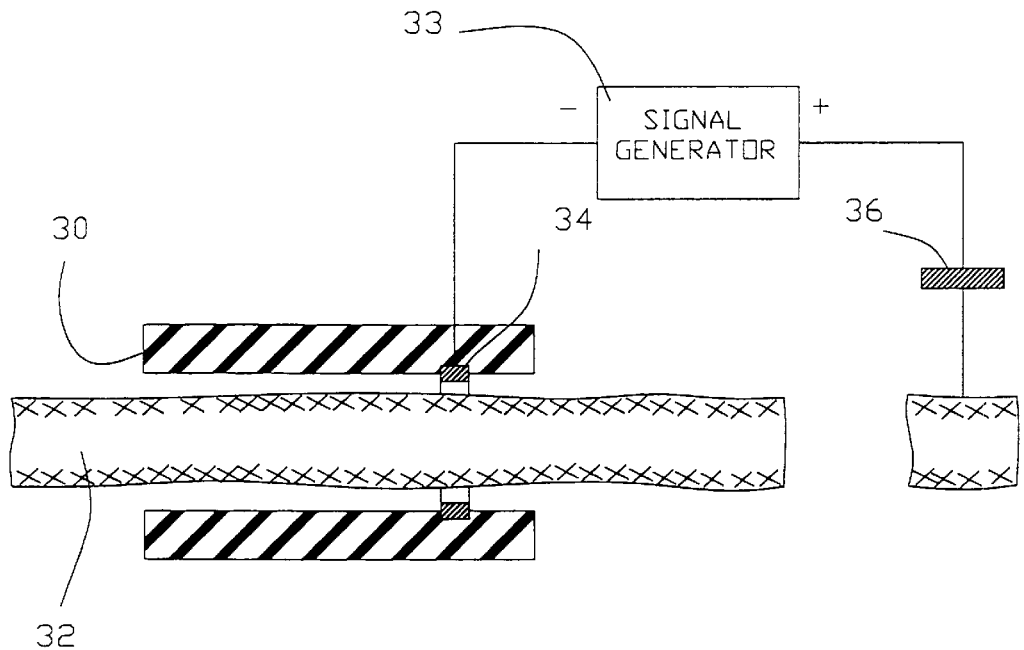
FIG. 2 is a perspective view showing an electrode cuff to be used with the present invention.

Waveform 10 is typically applied to a single nerve trunk using an arrangement which is shown in FIG. 2. Referring now to FIG. 2, an electrode cuff 30 is positioned about a nerve 32. A signal generator 33 is coupled to cuff 30 via a first electrode 34 located along the inner surface of cuff 30, and also to nerve 32 via a second electrode 36. In operation, electrode 34 acts as a cathode for signals transmitted from generator 33 to nerve 32, while electrode 36 acts as an anode for the circuit. In this manner, nerves can be stimulated externally using pulses transmitted by generator 33 through anode 36 and cathode 34.

Figure 3:
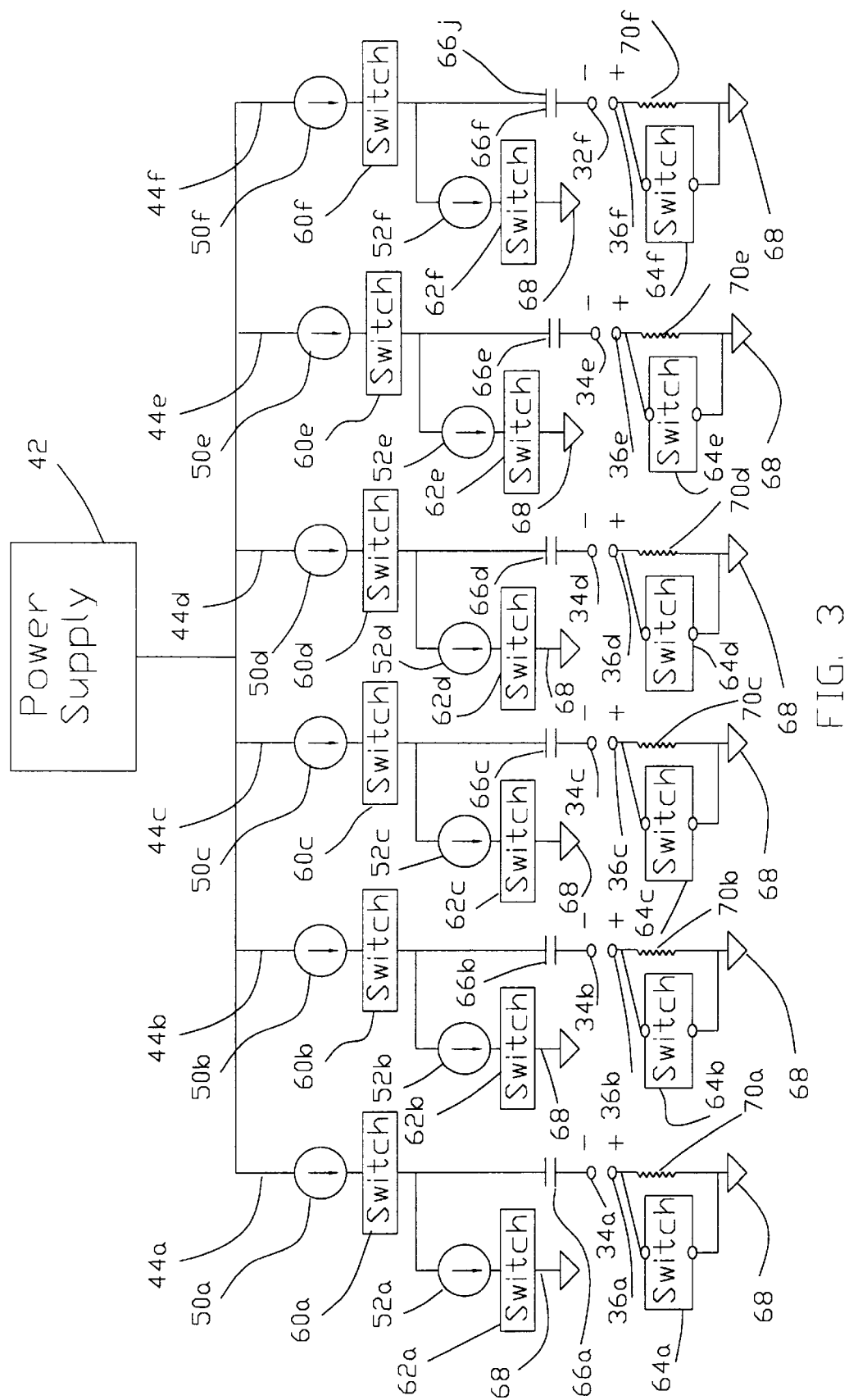
FIG. 3 is a block diagram of a multiple channel nerve stimulator circuit according to the present invention.

Referring more particularly to FIG. 3 of the drawings, the basic operating principle of the stimulator of the present invention can be explained. Stimulator 40 uses a single power supply 42 which drives a plurality of channels 44. In the present embodiment, six channels 44a–f are shown. The output stage of each channel 44 is connected to each electrode cuff 30 (as shown in FIG. 2) which is used to stimulate a sacral root in the nerve trunk of a patient in the manner described in U.S. Pat. No. 4,608,985, which patent is hereby incorporated by reference into this application. The electrode cuff 30 is connected between anode 36 and cathode 34 for each channel 44.

Each channel 44 contains two independent current sources 50 and 52 connected to cathode 34. Current sources 50 and 52 are responsible for generating the two phases of quasitrapezoidal signal 10 which is shown in FIG. 1, which is applied to the nerve. The operation of current sources 50 and 52 are controlled by a waveform generator 54 (FIG. 4) to generate signal 10, which signal is biphasic and charge balanced in order to minimize electrode deterioration and tissue damage.

Each channel 44 contain a series of switching means 60, 62, 64. Switching means 60, which couples current source 50 to current source 52 and to cathode 34 via a capacitor 66, and switching means 62, which couples current source 52 to a ground loop 68, are controlled by generator 54 to activate current sources 50 and 52 at the proper times in order to generate the proper waveform 10, while switching means 64 is connected in parallel with an isolation resistor 70 between anode 36 and ground loop 68.

Figure 4:
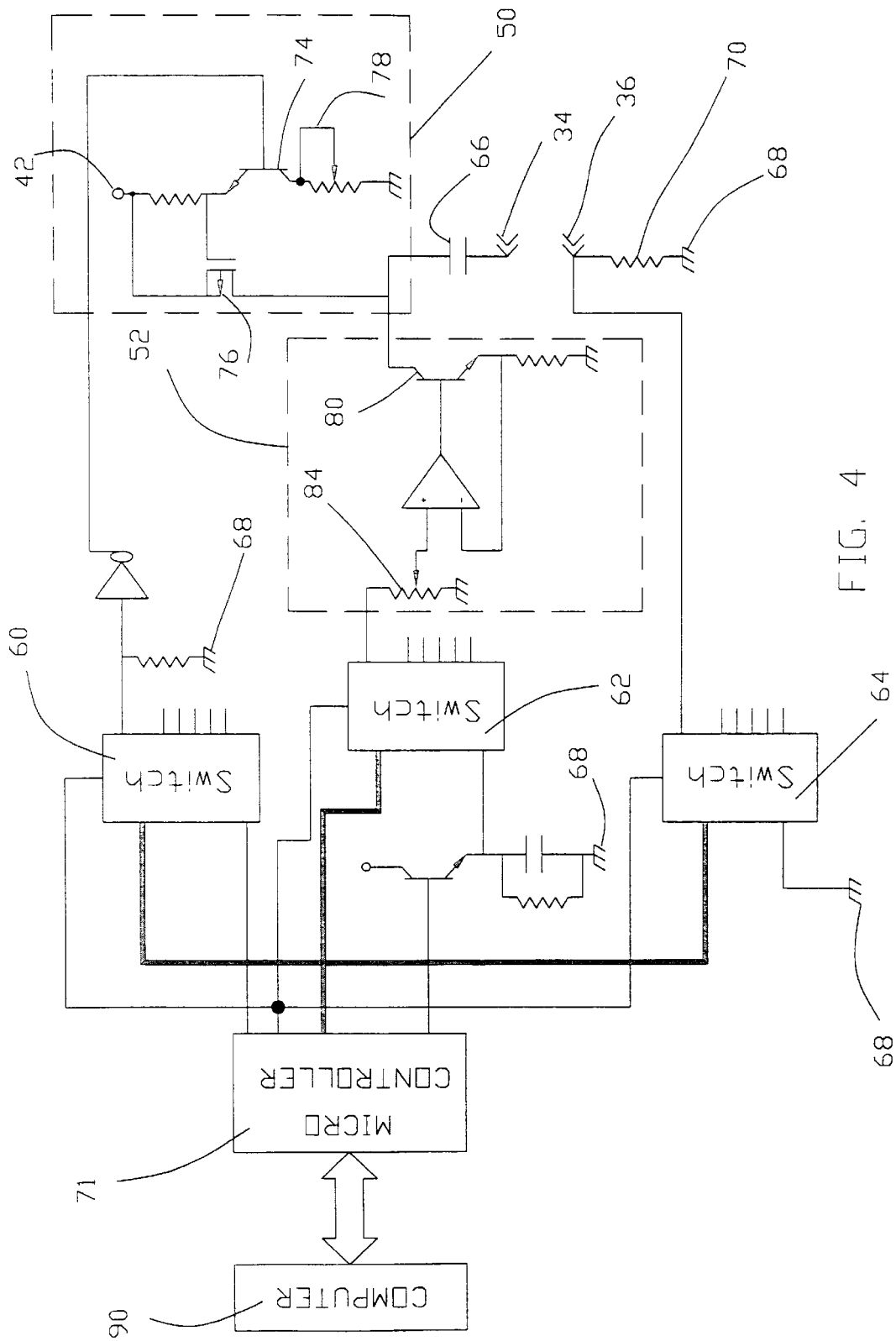
FIG. 4 is a block diagram of the stimulator circuit of FIG. 1 showing the controlling circuitry and one channel of the device in greater detail.

FIG. 4 shows a representation of stimulator 40 according to the present invention in greater detail. As can be seen in FIG. 4, current sources 50 and 52, along with switching means 60, 62 and 64 are all under complete control of a microcontroller 71 which handles the task of controlling the timing between all of the components of stimulator 40, and generates signal 10 by activating and inactivating current sources 50 and 52 and isolation resistors 70 in the proper timing sequence.

In operation, current source 50, which is composed of a transistor 74 and a PMOSFET 76 in combination, is initially activated by switch 60. In this embodiment, switching means 60 is preferably a multiplexer which is capable of controlling all of the channels for stimulator 40. The amplitude of current source 50 is controlled by a potentiometer 78. Current source 52, which is composed of a transistor 80 and an OP-AMP 82 in combination, is controlled by switching means 62, which is preferably a multiplexer capable of controlling all of the channels in the present embodiment. The amplitude of current source 52 is also controlled by a potentiometer 84. In the present embodiment, potentiometers 78 and 84 are preferably digital devices which are set electronically by microcontroller 71. Switching means 64, which is also preferably a multiplexer in the present embodiment, acts to shunt isolation resistor 70 to ground a when that specific channel 44 is active. In this way, the active channel 44 is shorted to ground loop 68, providing a path of zero resistance to the stimulus current, while the isolation resistors 70 in all of the other channels provide a high resistive path to the stimulus current, insuring that any leakage current will be minimized such that it will not affect the operation of stimulator 40.

Figure 5:
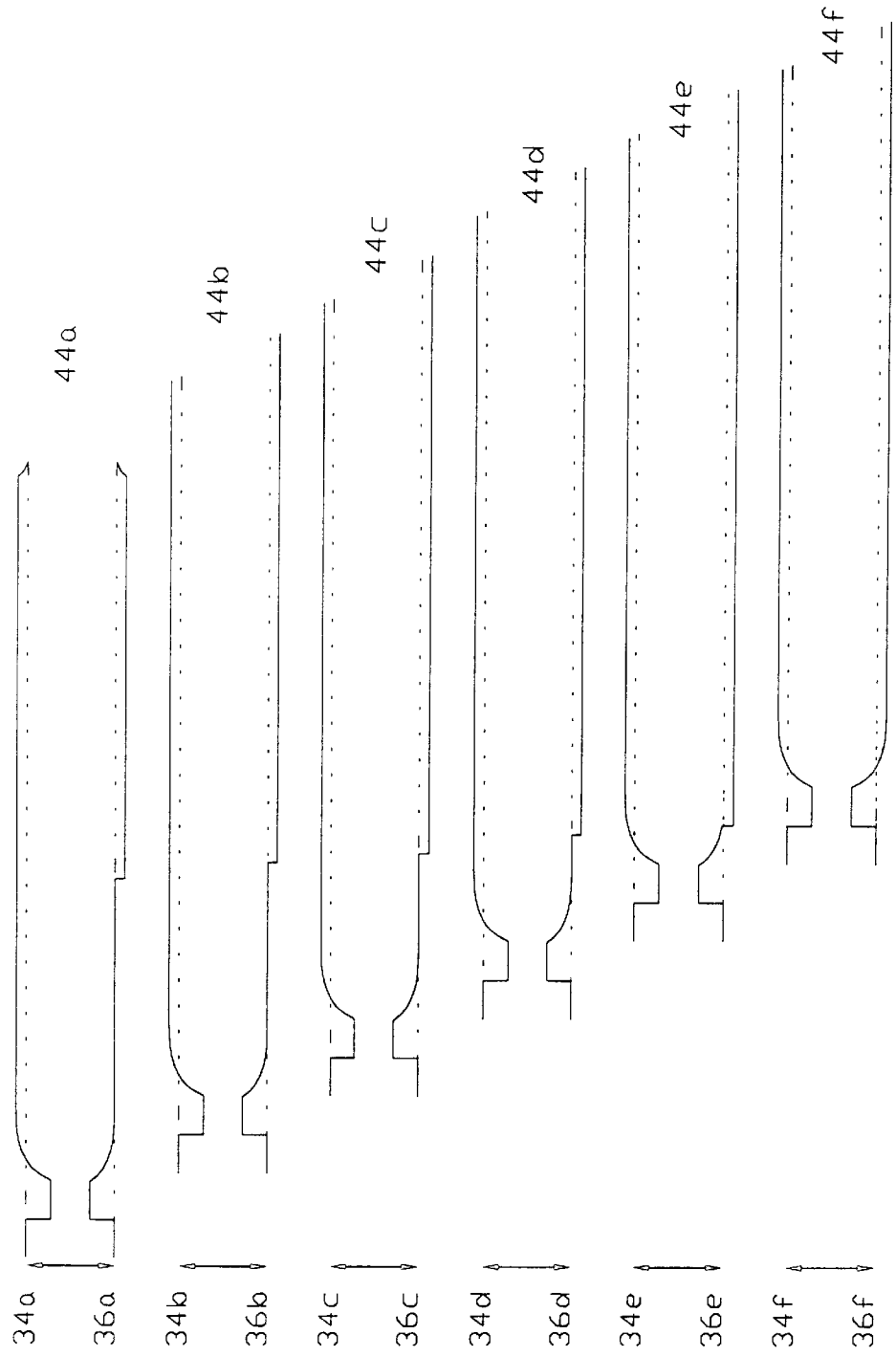
FIG. 5 is a timing diagram showing the outputs of the multiple channels of the device according to the present invention.

FIG. 5 shows the timing diagram associated with one firing sequence of stimulator 40. Referring now to FIG. 5, there is shown the waveforms generated by a six-channel stimulator having output channels 44*a*–44*f*. In this design, the outputs are fired sequentially in reference to the first phase of the stimulus. Each channel 44 starts the first phase of its stimulus after the previous one has finished. This is true for both cathode 34 and anode 36 outputs and is designed to minimize the interference between channels.

As can be seen in FIG. 5, the cathode 34 outputs for all of the channels 44 are identical. However, the anode 36 outputs differ in the reversal phase of waveform 10 for each channel 44. This difference is due to the isolation resistor 70 and multiplexer switching circuit 64 in each channel 44. When a specific channel of channels 44*a*–*f* is activated, that particular isolation resistor 70 is shorted by multiplexer 64 to ground loop 68, providing a path of zero resistance to the stimulus current. The isolation resistors in the other channels are maintained intact, providing a high resistance path to the stimulus current. Thus, the current will flow mainly through the active channel while limiting the current in the other channels. The small amounts of currents that may escape isolation occur during phase 2 of waveform 10 of the active channel. These currents flow from cathode 34 outputs of the other channels into cathode 34 output of the active channel instead of flowing into their respective anode 36 outputs. Therefore, anode 36 outputs of the other channels receive less amounts of currents during that time, which is seen in reduced reversal phase of waveform 10 for those outputs (FIG. 5). The reversal phase of waveform 10 of anode 36 outputs of the other channel is restored after all channels have finished being activated. A circuit without isolation resistor 70 would allow current to flow from all anode 36 outputs during the activation of a single channel 44, creating cross currents between the channels.

Figure 6:
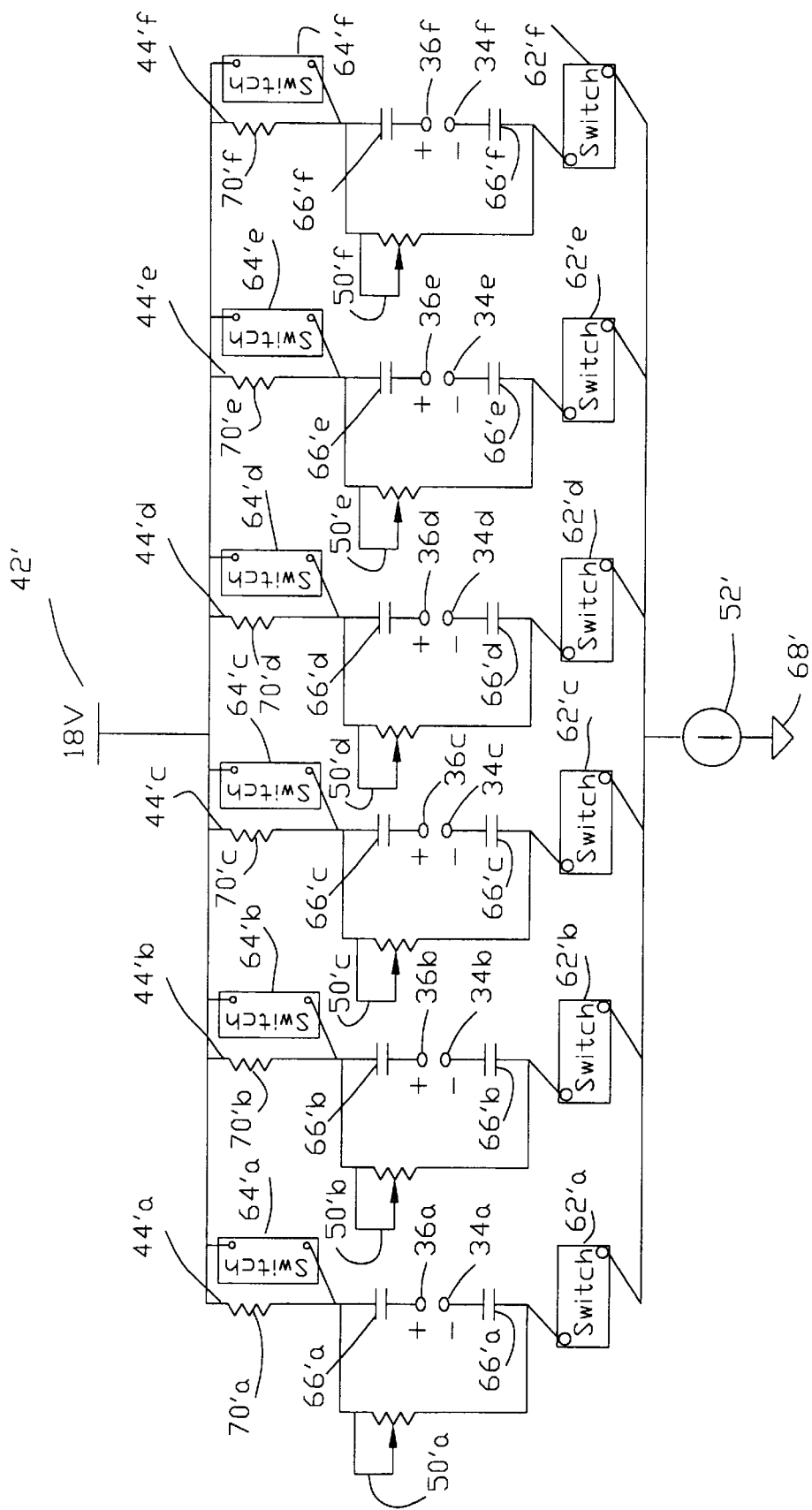
FIG. 6 is a block diagram of an alternative embodiment of a multiple channel nerve stimulator circuit according to the present invention.
Figure 7:
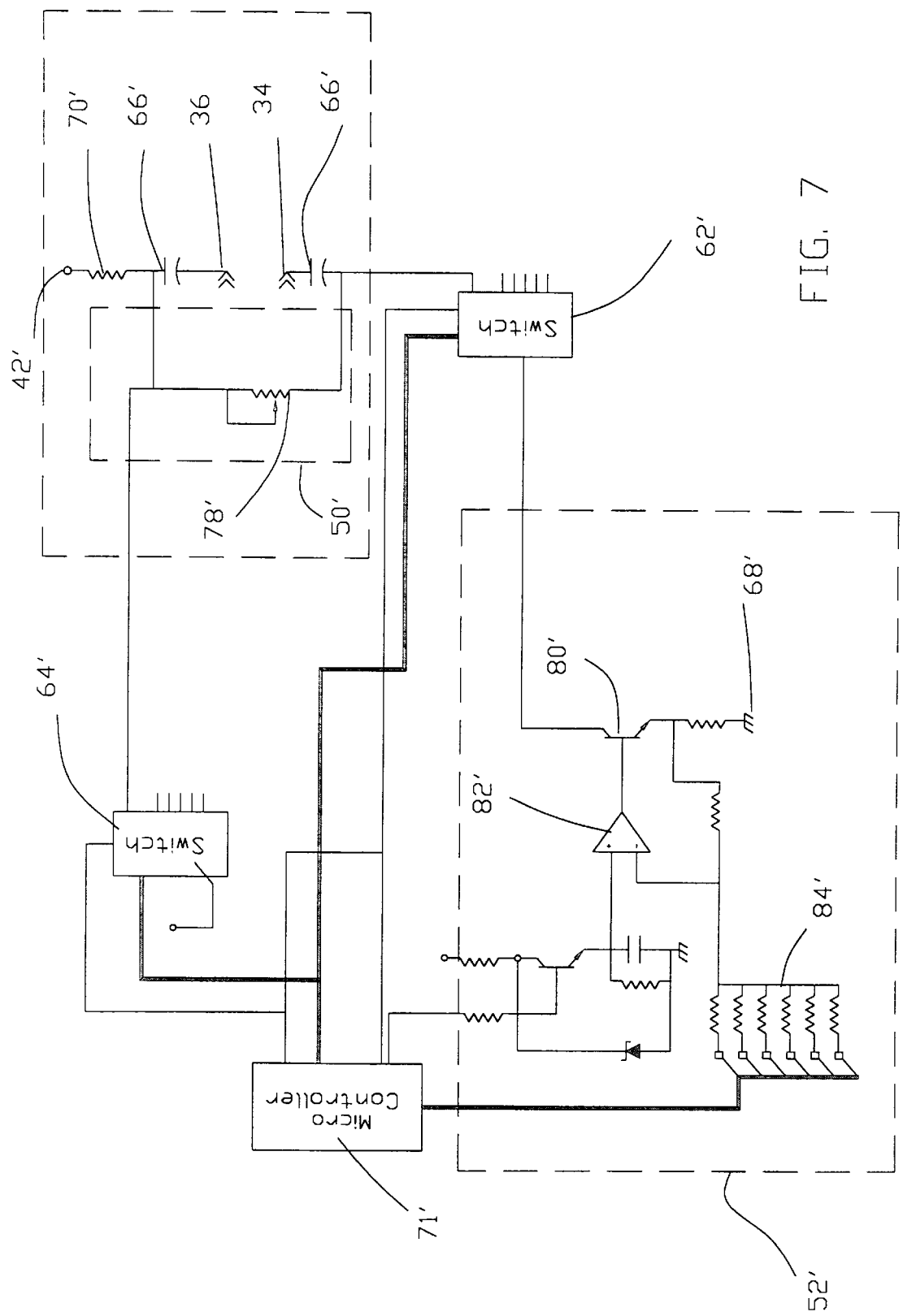
FIG. 7 is a block diagram of the stimulator circuit of FIG. 6 showing the controlling circuitry and one channel of the device in greater detail.
Figure 8:
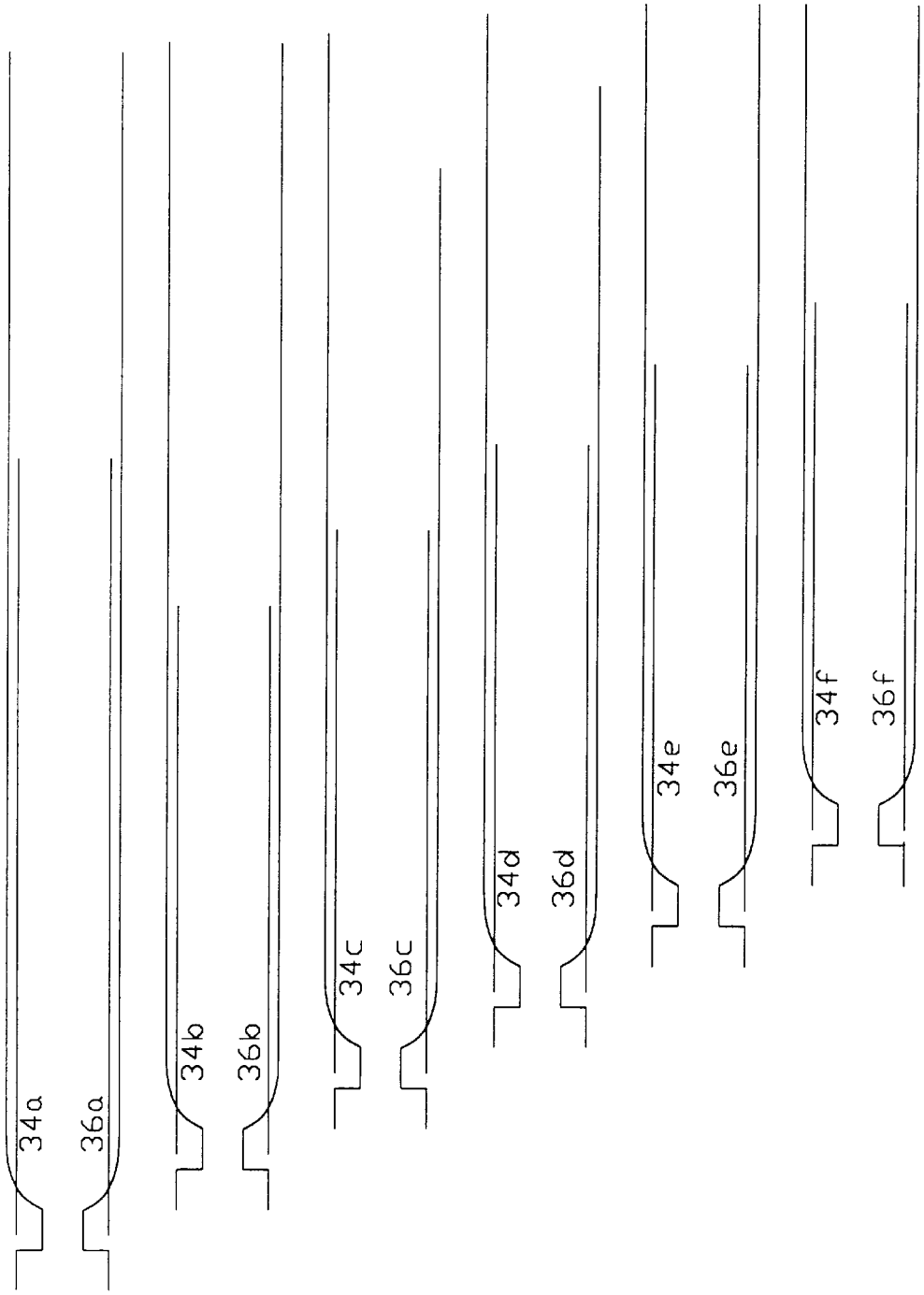
FIG. 8 is a timing diagram showing the outputs of the multiple channels of the device of FIG. 6.

An alternative design of nerve stimulator according to the present invention is shown in FIGS. 6–8. Referring more particularly to FIG. 6 of the drawings, the basic operating principle of the alternative stimulator embodying the present invention can be explained. Stimulator 40' uses a single power supply 42', which drives a plurality of channels 44'. In the present embodiment, six channels 44'*a*–*f* are shown. The output stage of each channel 44' is connected to each electrode cuff 30 (as shown in FIG. 2) which is used to stimulate a sacral root in the nerve trunk of a patient in the manner described in U.S. Pat. No. 4,608,985, which patent is hereby incorporated by the reference into this application. The electrode cuff 30 is connected between anode 36 and cathode 34 for each channel 44'.

There is one current source 52' common to all channels connected to cathode 34*a*–*f* through a switching means 62'. Current source 52' is responsible for generating the first phase of the quasitrapezoidal signal 10, which is shown in FIG. 1, which is applied to the nerve. The operation of current source 52' is controlled by the microcontroller 71. The second phase of signal 10 is created by the passive circuit 50'. Both current source 52' and passive circuit 50' are responsible for generating both phases of signal 10 which is biphasic and charge balanced in order to minimize electrode deterioration and tissue damage.

Each channel 44' contains a series of switching means 62' and 64'. Switching means 62' couples the current source 52' to the ground loop 68', while switching means 64' is connected in parallel with an isolation resistor 70' between capacitor 66' and power supply 42'. Switching means 62' and 64' are turned on and off concurrently, which directs the flow of current to one particular channel.

FIG. 7 shows a representation of stimulator 40' according to the present invention in greater detail. As can be seen in FIG. 7, current source 52', along with switching means 62' and 64' are all under complete control of a microcontroller 71' which handles the task of controlling the time between all of the components of stimulator 40', and generates signal 10 by activating and inactivating current source 52' and isolation resistors70' in the proper timing sequence.

In operation, current source 52', which is composed of transistor 80' and op-amp 82' in combination, has output that is distributed by switching means 62', which is preferably a multiplexer capable of controlling all of the channels in the present embodiment. The amplitude of current source 52' is controlled by a resistor array 84', which is under direct control of the microcontroller 71'.

Switching means 64', which is also preferably a multiplexer in the present embodiment, acts to shunt isolation resistor 70' to power supply 42' when that specific channel 44' is, active. In this way, the active channel 44' is shorted to power supply 42', providing a path of zero resistance to the stimulus current, while the isolation resistors 70' in all of the other channels provide a high resistive path to the stimulus current, insuring that any leakage current will be minimized such that it will not affect the operation of stimulator 40'.

When a particular channel 44' has finished being activated, current flows in the opposite direction through capacitors 66' and potentiometer 78'. The amplitude of this reversal current is controlled by adjusting potentiometer 78'. This reversal current represents portion 14 of waveform 10 and its path is restricted in its own output channel since switching means 62' and 64' are no longer connected to that channel. Switching means 62' and 64' will not be connected to that channel until that point of time when that channel needs to be activated again.

FIG. 8 shows the timing diagram associated with one firing sequence of stimulator 40'. Referring now to FIG. 8, there is shown the waveforms generated by a six channel stimulator having output channels 44'*a*–44'*f*. In this design, the outputs are fired sequentially in reference to the first phase of the stimulus. Each channel 44' starts the first phase of its stimulus after the previous one has finished. This is true for both cathode 34 and anode 36 outputs and is designed to minimize the interference between channels.

The design of the present invention was developed in a way that utilizes minimal hardware in order to maintain a small package size suitable for implantable use.

While the present invention has been shown and described in terms of a preferred embodiment thereof, it will be understood that this invention is not limited to any particular embodiment and that many changes and modifications may be made without departing from the true spirit and scope of the invention as defined in the appended claims.

What is claimed is:

1. A multiple channel stimulator for applying electrical impulses to nerves of a mammal, said stimulator comprising:
   a single power supply;
   at least two channel circuits, coupled to said power supply, for applying electrical impulses to a nerve of a mammal in order to stimulate said nerve;
   and control means, coupled to said channel circuits, for selectively activating a particular channel circuit to stimulate the nerve associated with that channel circuit, wherein said control means further includes switching means for reducing the resistance in said active channel circuit such that any leakage current to said inactive channels is minimized.

2. The stimulator of claim 1, wherein each channel circuit comprises an electrode cuff for contacting a nerve, said cuff having an anode and a cathode, a first current source coupling said cathode to said power supply, and an isolation resistor for coupling said anode to ground.

3. The stimulator of claim 2, wherein said switching means selectively bypasses said isolation resistor in said active channel circuit to provide a direct path to ground from said cathode and thus minimize leakage current to said inactive channel circuits from said active channel.

4. The stimulator of claim 3, wherein said control means further comprises a microcontroller.

5. The stimulator of claim 4, wherein said switching means comprises a multiplexer which is controlled by said microcontroller.

6. The stimulator of claim 1, wherein each channel circuit comprises an electrode cuff for contacting a nerve, said cuff having an anode and a cathode, an isolation resistor coupling said power supply to said cathode, and a first current source coupling said anode to ground.

7. The stimulator of claim 6, wherein said switching means selectively bypasses said isolation resistor in said active channel circuit to provide a direct path from said power supply to said anode and thus minimize leakage current to said inactive channel circuits from said active channel.

8. The stimulator of claim 5, wherein said control means further comprises a microcontroller.

9. The stimulator of claim 8, wherein said switching means comprises a multiplexer which is controlled by said microcontroller.

10. A multiple channel stimulator for applying electrical impulses to nerves of a mammal, said stimulator comprising:
    a single power supply;
    a plurality of channels, each connected to said power supply, for selectively applying electrical impulses to nerves of a mammal in order to stimulate said nerve;
    a plurality of cuff electrodes, each having an anode and a cathode, coupled to each channel and adapted to contact the nerve associated with said channel;
    and control means, coupled to said plurality of channels, for selectively activating a particular channel to stimulate the nerve associated with that channel, wherein said control means further includes first switching means for coupling said anode associated with said selected channel to ground to provide a path of zero resistance, whereby leakage current between said selected channel and other channels is minimized.

11. The stimulator of claim 10, wherein each channel further comprises a first current source coupled between said power supply and said anode, and a second current source coupled between said first current source and ground.

12. The stimulator of claim 11, wherein said control means further comprises second and third switching means which operate said first and second current sources to generate a waveform which is transmitted to said selected nerve through said cuff electrode.

13. The stimulator of claim 12, wherein said generated waveform is a quasitrapezoidal pulse.

14. The stimulator of claim 12, wherein said control means comprises a microcontroller and said first, second, and third switching means comprise multiplexers.

15. A multiple channel stimulator for applying electrical impulses to nerves of a mammal, said stimulator comprising:
    a single power supply;
    a plurality of channels, each connected to said power supply by an isolation resistor, for selectively applying electrical impulses to nerves of a mammal in order to stimulate said nerve;
    a plurality of cuff electrodes, each having an anode and a cathode, coupled to each channel and adapted to contact the nerve associated with said channel;
    and control means, coupled to said plurality of channels, for selectively activating a particular channel to stimulate the nerve associated with that channel, wherein said control means further includes first switching means for coupling said anode associated with said selected channel directly to said power supply and bypassing said isolation resistor, whereby any leakage current between said selected channel and other channels is minimized.

16. The stimulator of claim 15, wherein said power supply is coupled to the cathodes of said electrodes through a first current source.

17. The stimulator of claim 16, wherein said control means further comprises a variable resistance connected between said anode and cathode of each cuff electrode, and second switching means which operate said variable resistance and said first current source to generate a waveform which is transmitted to said selected nerve through said cuff electrode.

18. The stimulator of claim 17, wherein said generated waveform is a quasitrapezoidal pulse.

* * * * *